(12) United States Patent
Roos

(10) Patent No.: US 7,320,753 B2
(45) Date of Patent: Jan. 22, 2008

(54) ANAEROBIC DIGESTER SYSTEM FOR ANIMAL WASTE STABILIZATION AND BIOGAS RECOVERY

(75) Inventor: Kurt Frederich Roos, Dumfries, VA (US)

(73) Assignee: The United States of America as represented by the United States Environmental Protection Agency, Washington, DC (US)

( * ) Notice: Subject to any disclaimer, the term of this patent is extended or adjusted under 35 U.S.C. 154(b) by 0 days.

(21) Appl. No.: 11/682,086

(22) Filed: Mar. 5, 2007

(65) Prior Publication Data
US 2007/0256971 A1 Nov. 8, 2007

Related U.S. Application Data

(63) Continuation of application No. 11/381,967, filed on May 5, 2006, now Pat. No. 7,186,339.

(51) Int. Cl.
*C02F 3/28* (2006.01)
(52) U.S. Cl. ............ 210/603; 210/916; 435/262.5
(58) Field of Classification Search ........ 210/603, 210/609, 916; 71/10, 21; 435/262, 262.5
See application file for complete search history.

(56) References Cited

U.S. PATENT DOCUMENTS

| | | | |
|---|---|---|---|
| 4,100,023 A * | 7/1978 | McDonald | 435/167 |
| 4,157,958 A | 6/1979 | Chow | |
| 4,169,048 A * | 9/1979 | Albers, Sr. | 210/603 |
| 4,436,818 A * | 3/1984 | Widmer | 435/290.2 |
| 4,579,654 A * | 4/1986 | Bremmer | 210/180 |
| 4,692,249 A | 9/1987 | Hammel | |
| 5,080,786 A | 1/1992 | De Lima | |
| 5,221,570 A | 6/1993 | Gokcen et al. | |
| 6,296,766 B1 | 10/2001 | Breckenridge | |
| 2003/0078552 A1* | 4/2003 | Tepper et al. | 604/333 |
| 2005/0130290 A1* | 6/2005 | Choate et al. | 435/262 |

FOREIGN PATENT DOCUMENTS

JP 62-32875 * 2/1987

OTHER PUBLICATIONS

Gas Bio-Digester Information and Construcion Manual for Rural Families, FUCOSOH, Laura Brown (2004).*

(Continued)

*Primary Examiner*—Fred G. Prince
(74) *Attorney, Agent, or Firm*—Weiss & Moy PC; Janine R. Novatt

(57) ABSTRACT

An ambient anaerobic digester system for anaerobic digestion of animal waste with biogas production and recovery is provided. The anaerobic digester system includes a substantially flexible bladder for anaerobically digesting the animal waste with biogas production and transmitting the biogas to at least one biogas storage container, biogas use device or a combination thereof. In a preferred form, the substantially flexible bladder has a waste inlet, a digester effluent outlet, one or more sludge access ports and a biogas outlet in a top surface thereof. The anaerobic digester system may inexpensively, simply, reliably, and effectively be used to treat animal waste without energy expenditure and little capital expense, thus minimizing pollution typically caused by animal waste.

15 Claims, 8 Drawing Sheets

OTHER PUBLICATIONS

Agstar Charter Farm Program: Experience With Five Floating Lagoon Covers, Presented at the Fourth Biomass Conference of the Americas, Roos et al. (1999).*

Brown, Gas Bio-digester Information and Construction Manual for Rural Families, FUCOSOH, Nov., 2004.

Roos et al., Agstar Charter Farm Program: Experience with Five Floating Lagoon Covers, Fourth Biomass Conference of the Americas, Oakland, CA, Aug. 29-Sep. 2, 1999.

* cited by examiner

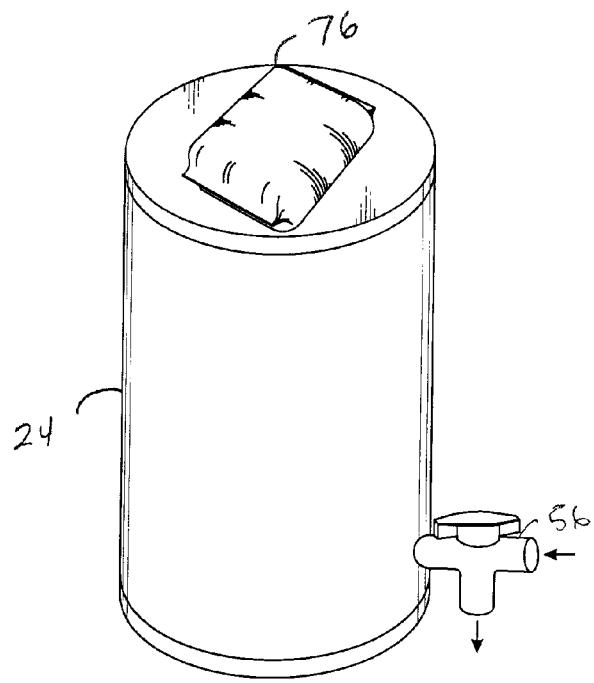
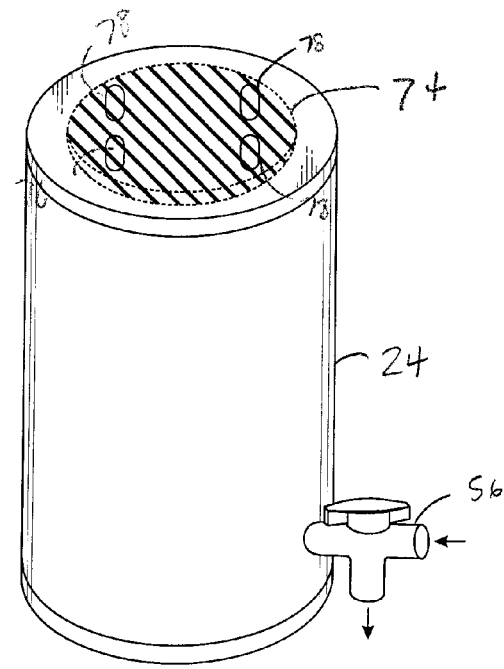
Fig. 6  Fig. 6A
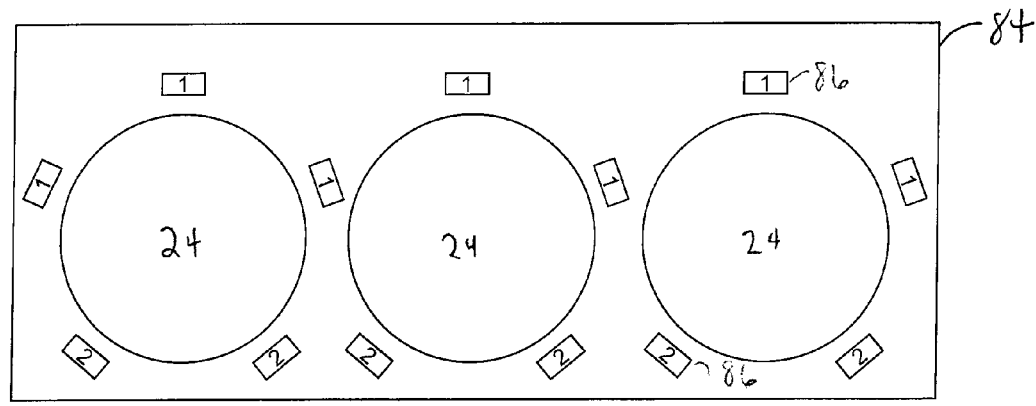
Fig. 7

ANAEROBIC DIGESTER SYSTEM FOR ANIMAL WASTE STABILIZATION AND BIOGAS RECOVERY

CROSS-REFERENCE TO RELATED APPLICATION

This patent application is a continuation of U.S. Ser. No. 11/381,967 filed May 5, 2006 (now U.S. Pat. No. 7,186,339 issued Mar. 6, 2007), having the same title and in the name of the same inventor as the present application and is hereby incorporated into the present patent application.

FIELD OF THE INVENTION

This invention relates to pollution control and more specifically, to an improved anaerobic digester system for animal waste treatment with biogas production and recovery.

BACKGROUND OF THE INVENTION

Livestock confinement facilities generate large amounts of animal waste that can create serious environmental and human health concerns. For example, animal waste constituents such as organic matter, nitrogen, phosphorus, pathogens and metals can degrade water quality, air quality, and adversely impact human health. Organic matter, for example, contains a high amount of biodegradable organics and when discharged to surface waters will compete for, and deplete the limited amount of dissolved oxygen available, causing fish kills and other undesirable impacts. Similarly nutrient loading from nitrogen and phosphorus can lead to eutrophication of surface waters. Thus, in the United States through the Clean Water Act and in other developed countries, animal waste may not be discharged but terminally applied to land as a supplement to commercial fertilizer. These requirements do not exist in many other countries having large numbers of livestock and thus, animal waste adversely impacts environmental quality. For example, there is growing evidence of water pollution caused by the discharge of livestock waste into surface waters in various global watersheds and there is now evidence of these discharges affecting coastal water quality such as in the South China Sea, the Gulf of Thailand, and in the Gulf of Mexico.

Animal wastes also impact air quality, which include odor and greenhouse gas emissions. Wastes also contain viruses, bacteria, protozoa, and helminthes that when transmitted to humans can adversely impact human health in a number of ways some of which are life threatening.

A variety of technical approaches have been used to abate these concerns to varying degrees. At the most basic level, wastes are stored and land applied at agronomic rates to reduce nutrient loading and run-off potential. However manure storage does not stabilize waste and therefore does not reduce odor, pathogens, or oxygen demanding materials. More complex processes may use a combination of pre-treatment, primary, secondary, and tertiary treatment processes to provide comparatively superior levels of managing environmental and human health related concerns. Primary treatment is an essential first step when secondary and tertiary processes are considered as primary treatment reduces oxygen demand, reduces pathogens, converts nitrogen and phosphorus into plant available forms, specifically ammonia N and phosphate. Plant available forms of nutrients ensure uptake with a high level of predictability when applied at agronomic rates relative to crop type.

Typically anaerobic processes are used in primary treatment of livestock and other high strength organics as they are economically desirable when compared to aerobic methods. Anaerobic processes transform manure into a variety of end products, including digester effluent and biogas. Various anaerobic systems have been used commercially depending on livestock type, climate and water usage.

One of the most common anaerobic systems used for the treatment of dilute manure is an anaerobic treatment lagoon. In lagoons or any other unmixed systems, materials stratify into solid and liquid components. Sludge (biologically degraded solids) accumulate at the bottom of the lagoon and is composed of settled non-biodegradable and fixed constituents of manure, and active and dead microbial cells. Sludge is black, moderately viscous, typically about 10 percent solids and 90 percent liquid, and high in nutrients, bacteria, and organic matter. Sludge is the byproduct of biological anaerobic degradation or the biodegradable component of organic material. Sludge can be removed manually or by pumps designed for higher solids applications i.e., 10 to 15 percent solids.

The layer above the sludge is the liquid layer. This liquid, the digester effluent, is low in solids (generally 0.3 to 0.6 percent solids), moderately rich in nutrients and easily pumped with irrigation pumps. If the liquid and sludge are mixed, the solids content will range between <1 percent and 8 percent solids, depending on the proportion of process water, rainfall and sludge in the system. The digester effluent and sludge will contain all of the remaining (that which is not volatilized to air) nitrogen, phosphorus, potassium, micronutrients, and metals in the original manure. These can be further processed or land applied.

Unfortunately, anaerobic treatment lagoons while effective in stabilizing organics, are open systems and can emit odor, volatile organic compounds (VOC's), and a number of other constituents into the air that are of growing concern. These gases consist of methane, a greenhouse gas with a warming potential 23 times that of carbon dioxide; ammonia and VOC's which are prerequisite gases in the formation of fine particulate matter (smog), and hydrogen sulfide, an odor compound, which can also cause death in high concentrations. However, when this biogas consisting of about 70% methane is captured in various types of anaerobic digesters and utilized for its energy value, it can provide financial benefit by offsetting energy costs while reducing the air impacts by various combustion processes that destroy methane and hydrogen sulfide.

This biogas can be burned for heat or used to fuel an electric generator among other uses. The heat and electricity can be used on the farm or sold to others. As used herein, a "continuous biogas system" refers to the continuous feeding of biogas to a biogas combustion device such as flares and engines for operation thereof. A "stored biogas system" refers to the storage of biogas for intermittent combustion and use.

There are a myriad of anaerobic digester systems and scales in use around the world. These include simple unheated systems such as covered lagoons and more complex systems that are heated to about 100° F. or higher. Maintaining higher constant temperature reduces reactor volumes required to treat and stabilize waste. A conventional anaerobic digester system generally includes the following components: manure transfer and mixing pit, a digester made of steel, fiberglass, concrete, earth or other suitable material (including heating and mixing equipment if needed), biogas handling and transmission, and gas end use (combustion) equipment such as electric generation equipment. Conventional anaerobic digesters can also require significant operational oversight depending on operational mode and temperature. Conventional anaerobic digester systems also require proper design and sizing to maintain critical bacterial populations responsible for waste treatment and stabilization for sustained long-term predictable performance. Sizing requirements are based on hydraulic retention time (HRT), and loading rate where the operating temperature affects these sizing parameters. These factors (size, materials, operational requirements) affect digester costs, which may be fairly capital intensive and in some economies and farm scales may not be affordable or may be inoperable if experienced technicians are not available.

The issues of affordability and operational ability are exacerbated in developing countries or countries with economies in transition. These countries are predominantly located between 350 north and south latitude where the range of farm scales may be very small household farms to very large corporate production oriented types of farms. This range may encompass farm scales of 5-100,000 pigs or 1-10,000 milk cows per facility. These regions are also showing signs of severe environmental degradation, particularly water and human health, due to large population growth and concentration. These regions to various extents have promoted various anaerobic digesters operated at ambient temperatures constructed from an array of locally available materials to control costs and more expensive and operationally complex systems for larger scale farms. In many cases these smaller systems use low quality materials of limited durability and lifetime to control cost and the larger scale systems may not be cost effective or transportable. Moreover the sizing methodologies used predominantly for smaller scale systems are based on reactor volumes to meet the daily gas requirements for a household or farm (biogas is about 20 cu. Ft/person/day). This approach typically results in only partially stabilizing the waste stream as bacterial populations are subject to washout, short circuiting, and/or excessive loading rates. Furthermore these systems accumulate solids with no provision for removal. Solids and/or sludge accumulation reduce reactor volume and HRT and increase the loading rate causing decreased gas production, increased $CO_2$ concentration in gas stream and/or system failure. The operating track record of these systems has shown marginal to poor performance. While the need to provide affordable technology in the marketplace is essential, it is also essential to integrate quality with performance that enhances the environmental and sanitary conditions for both human and animal health.

Accordingly, there has been a need for a novel improved anaerobic digester system and method for treating animal waste that are predictable, effective, durable, affordable, simple to operate, portable, labor efficient, environmentally friendly, and substantially reliable year-round in tropical and semi-tropical regions located between 35° north and south latitude where these areas have average ambient temperatures of about 65° F. or higher (when at sea level or slightly higher) for passive heating of the digester. There is a further need for a novel improved anaerobic digester and method for primary waste treatment and biogas production for the small, medium, and large scale farms. There is a still further need for a novel anaerobic digester system and method that may be combined with secondary and tertiary processes which increases its environmental performance relative to air, water and human health quality. There is an additional need for a novel improved anaerobic digester system and method that help control air and water pollution from livestock waste, protect public health and offer an opportunity for the waste to be used as a renewable energy resource. The present fulfills these needs and provides other related advantages.

SUMMARY OF THE INVENTION

The present invention is concerned with an anaerobic digester system comprising a substantially flexible bladder for anaerobically digesting animal waste, with biogas production and recovery. The substantially flexible bladder has one or more waste inlets, digester effluent outlets, sludge access ports, and biogas outlets on a top surface thereof. The anaerobic digester system may further comprise one or more biogas storage containers for receiving biogas from the substantially flexible bladder. The bladder and the one or more biogas storage containers may be constructed with reinforced geo-membrane material. The bladder may be sized to maintain critical bacterial populations for areas located between 35° north and south latitude where ambient temperatures are about 65 degrees Fahrenheit or higher and to accommodate varying waste volumes from livestock farms. The substantially flexible bladder may be portable, factory fabricated and field installed.

The bladder may include an internal baffle defining a U-shaped interior having an inlet side and an outlet side. The waste inlet and the one or more sludge access ports are defined in the inlet side of the bladder and the digester effluent port and one or more biogas outlets are defined in the outlet side of the bladder. Alternatively, the waste inlet and digester effluent outlets may be at opposite ends of the bladder.

The animal waste enters the bladder at the waste inlet and flows through the bladder and undergoes bacterial digestion before exiting through the digester effluent outlet for further processing or land application. The bladder, for primary waste treatment, may be complemented by other structures for secondary and tertiary waste treatments.

The one or more sludge access ports may be used to withdraw sludge from the bladder. A sludge drawdown tube may extend inwardly into the substantially flexible bladder from each of the sludge access ports. The sludge may be separate from the liquid fraction (i.e. the digester effluent) and either manually or mechanically removed through the one or more sludge access ports.

The biogas generated in the bladder from anaerobic digestion of the animal waste may be discharged through the biogas outlet to a biogas pipe for transmission to one or more biogas use devices and/or one or more biogas storage containers. Pressure within the bladder may be regulated through a manometer. A valve regulates the flow of biogas out of the bladder and into and out of the one or more biogas storage containers.

Where biogas may be sold, distributed and used off-site, the biogas storage containers may be portable. Alternatively, the biogas may be stored inside the bladder for use onsite. When used in this manner, the system further comprises an external displacement tank. The external displacement tank is designed to hold waste that is displaced by internal bladder pressure. As biogas is produced inside the bladder, the waste is pushed out of the digester effluent outlet into the external displacement tank and when biogas is used, the displaced waste flows back into the bladder through the digester effluent outlet.

Other features and advantages of the present invention will become apparent from the following more detailed description, taken in conjunction with the accompanying drawings which illustrate, by way of example, the principles of the invention.

BRIEF DESCRIPTION OF THE DRAWINGS

The accompanying drawings illustrate the invention. In such drawings:

FIG. 6 is a perspective view of an exemplary biogas storage container coupled to a ball valve, illustrating by arrows the transmission of biogas into and out of the biogas storage container;

FIG. 6A is another perspective view of the exemplary biogas storage container of FIG. 6 with a reinforcing wafer in a top portion thereof;

FIG. 7 is a top view of a supporting platform with flexible supports for storing a plurality of exemplary cylindrical biogas storage containers;

DETAILED DESCRIPTION OF THE PREFERRED EMBODIMENTS

Figure 1:
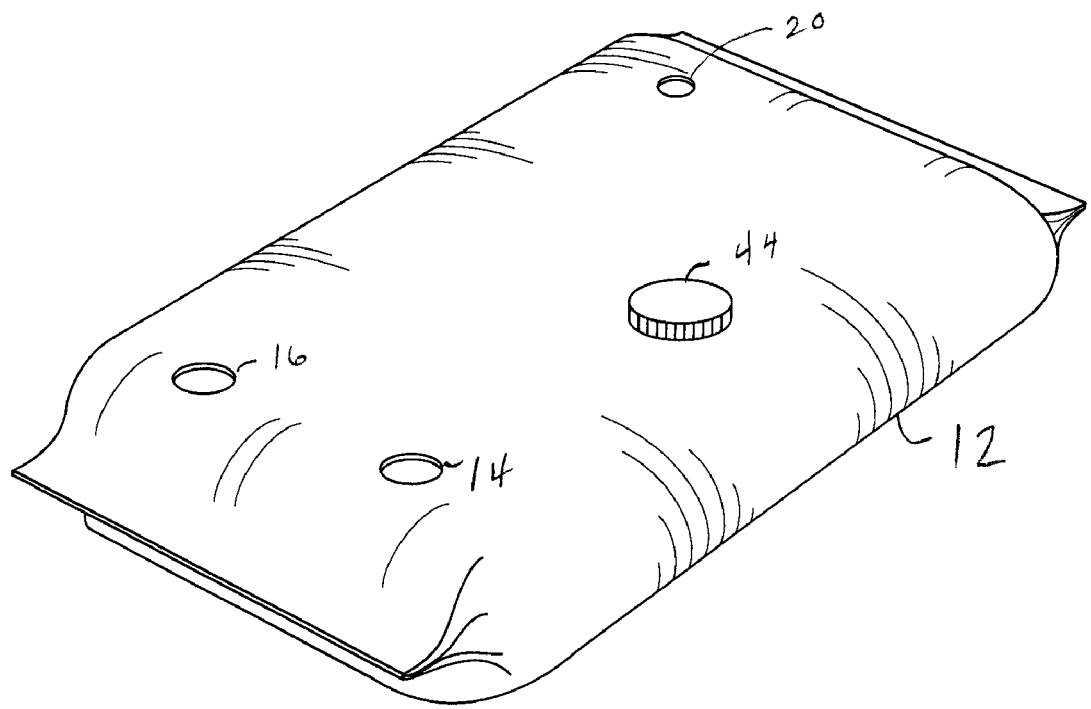
FIG. 1 is a perspective view of a substantially flexible bladder embodying the invention, illustrating the bladder having a waste inlet, a sludge access port, a digester effluent outlet, and a biogas outlet in a top surface thereof.

As shown in the drawings for purposes of illustration, the present invention is concerned with an improved anaerobic digester system for anaerobic digestion of animal waste with biogas production and recovery, the system generally designated in the accompanying drawings by the reference number 10. The anaerobic digester system comprises, generally, a substantially flexible bladder 12 and 120 constructed of a reinforced geo-membrane material for anaerobically digesting waste with biogas production having one or more waste inlets 14, digester effluent outlets 16, sludge access ports 18, and biogas outlets 20 in a top surface 22 thereof and sized to have a design operating volume based on latitude to maintain the greater of a selected maximum daily volatile solids (VS) loading rate per 1,000 ft$^3$, or the minimum hydraulic retention time (HRT) adequate for methane production. The anaerobic digester system 10 may further comprise one or more biogas storage containers 24 and 240 for receiving biogas from the substantially flexible bladder 12 and 120.

The bladder 12 or 120, for primary waste treatment, biologically stabilizes the animal waste. Biogas production is a byproduct of the anaerobic process. The biogas may be recovered as a renewable energy resource or delivered to combustion devices as an energy source or for air quality objectives such as flaring for odor or greenhouse biogas emission control to protect air quality.

As shown in FIG. 1, the bladder 12 and 120 comprises a substantially flexible bag having the top surface 22 and a bottom surface 26. The bladder 12 and 120 may be constructed of reinforced geo-membrane materials having the following approximate physical properties:

| PHYSICAL PROPERTY | TEST METHOD | STANDARD |
| --- | --- | --- |
| Thickness | ASTM D751 | 20-30 mils minimum |
| Tear Strength | ASTM D4533 Trapezoid Tear | 35 lbf minimum |
| Breaking Yield Strength | ASTM D751 Grab Tensile | 550/550 Lbf |
| Dimensional Stability | ASTM D1204 212° F.-1 hr | 1% maximum each direction |
| Adhesion Heat Sealed Seam | ASTM D751 Dielectric Weld | 35 lb$_f$/2 in minimum |
| Dead Load Seam Shear Strength | MIL-T-52983E (modified), Para. 4.5.2.19 | 2 in seam, 4 hrs, 1 in strip 210 lb$_f$ @ 70° F. 105 lb$_f$ @ 160° F. |
| Bursting Strength | ASTM D751 Ball Tip | 650 lb$_f$ Typical 800 lb$_f$ Typical |
| Adhesion-Ply | ASTM D2413 | |
| Puncture Resistance | ASTM D4833 | 50 lb$_f$ Typical |
| Tearing Strength, lbf | ASTM D5884 Tongue Tear | 55 min |
| Ozone Resistance, 100 pphm, 168 hours | ASTM D1149 | No cracks |
| Resistance to xenon-arc weathering[1] | ASTM G155 0.70 W/m$^2$ 80° C. B.P.T. | No cracks No loss of breaking or tearing strength |

ASTM = American Society for Testing and Materials incorporated herein by reference
[1]Approximately equivalent to 8000 hours exposure at 0.35 W/m$^2$ irradiance Suitable materials for the bladder include reinforced geo-membrane materials such as XR-5® 8130 or XR-3® 8228 reinforced geo-membranes available from the Seaman Corporation, Wooster, Ohio, and reinforced geo-membranes from Cooley Engineered Membranes, Pawucket, R.I. or the like. The materials may be reinforced with scrim material or the like. The material should be durable (puncture resistant), with high dimensional stability (about 1% maximum in each direction), and UV resistance. The minimum thickness for the geo-membrane material is about 20 mil.

The bladder may be factory fabricated with dielectric or wedge welding methods or similar type method to produce quality, non-leaking seams 28. The seam strengths may be within about 5-10% the tear strength of the material for a substantially gas tight seal. The bladder may be fabricated from materials that are compatible with such dielectric or wedge welding technologies.

Figure 3:
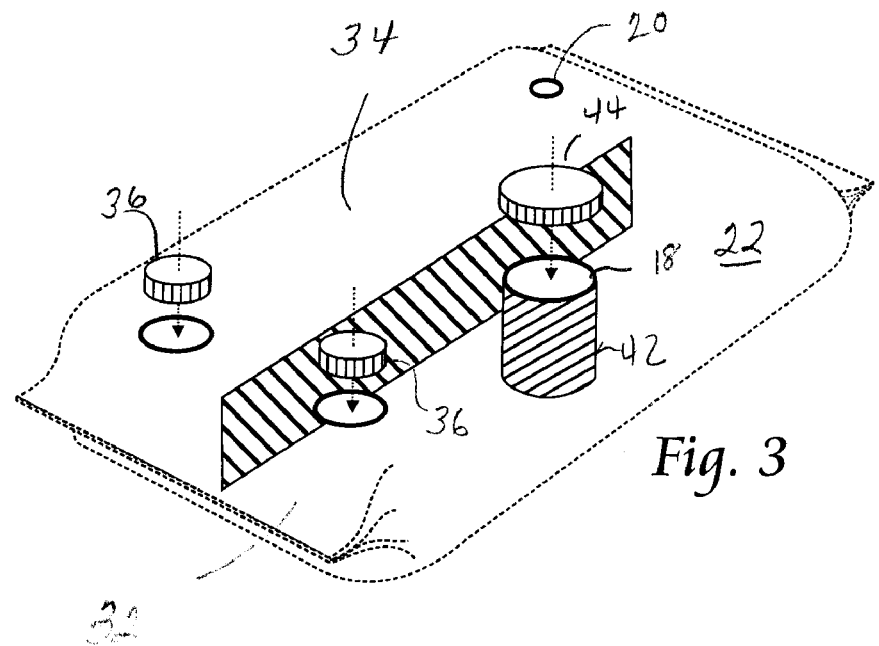
FIG. 3 is an interior perspective view of the bladder of FIG. 1, illustrating the bladder in dotted lines to show the interior thereof with a baffle between an inlet and an outlet side of the bladder and a sludge drawdown tube extending inwardly from the sludge access port and a substantially leak-proof cap thereon.
Figure 3A:
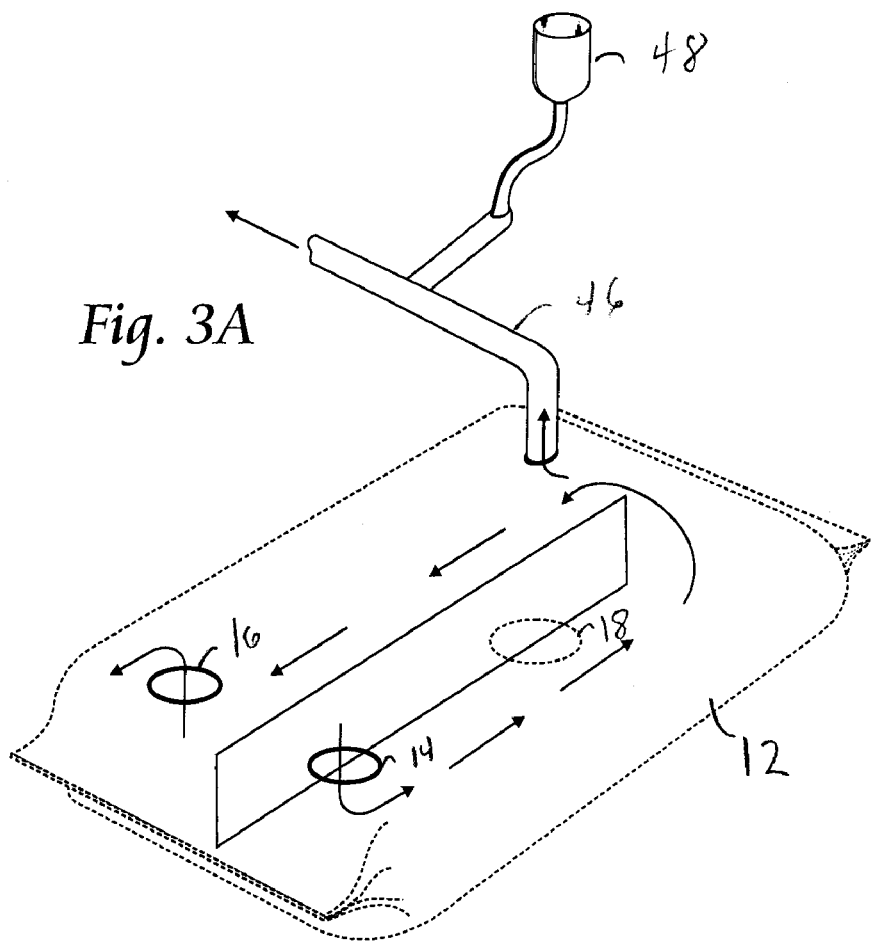
FIG. 3A is another interior operational perspective view of the bladder of FIGS. 1 and 3, illustrating by arrows the movement of animal waste (not shown) into the waste inlet and out the digester effluent outlet and release of biogas through a biogas outlet pipe connected to the exemplary manometer of FIG. 2.
Figure 3B:
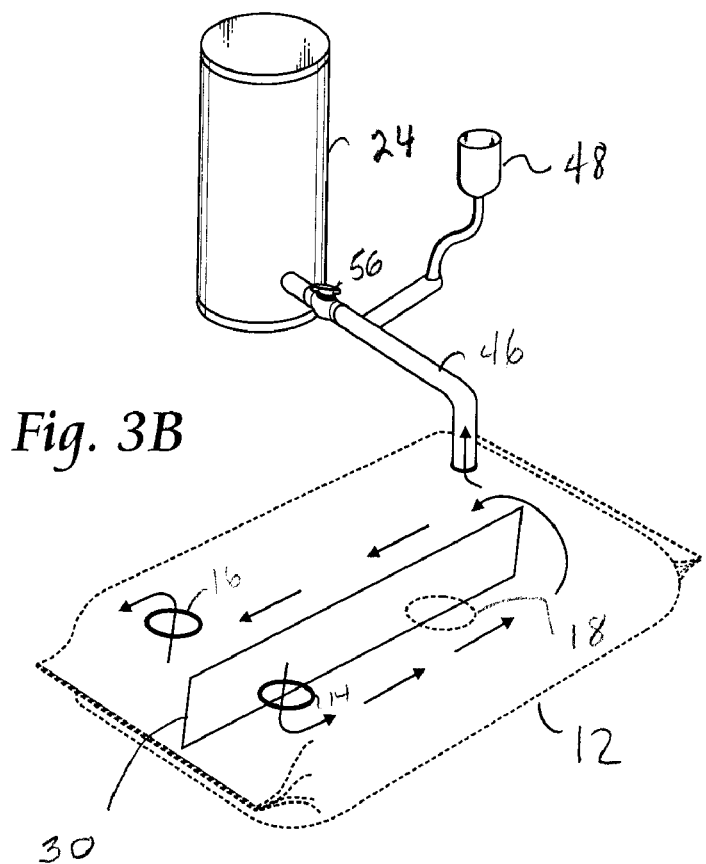
FIG. 3B is a similar view to FIG. 3A, illustrating transmittal of the biogas to an exemplary biogas storage container.
Figure 3C:
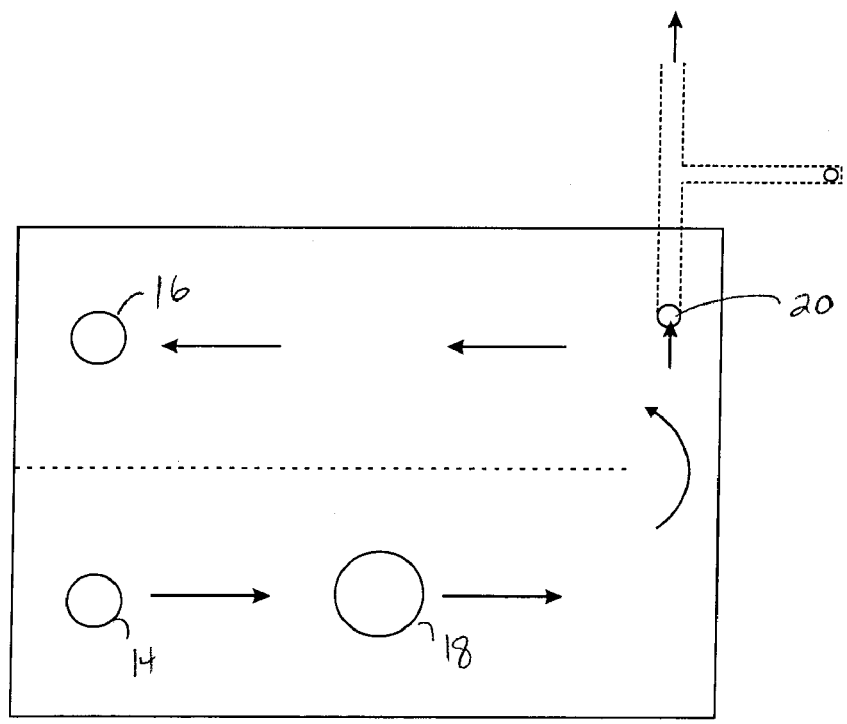
FIG. 3C is a top schematic view of FIG. 3A.
Figure 4:
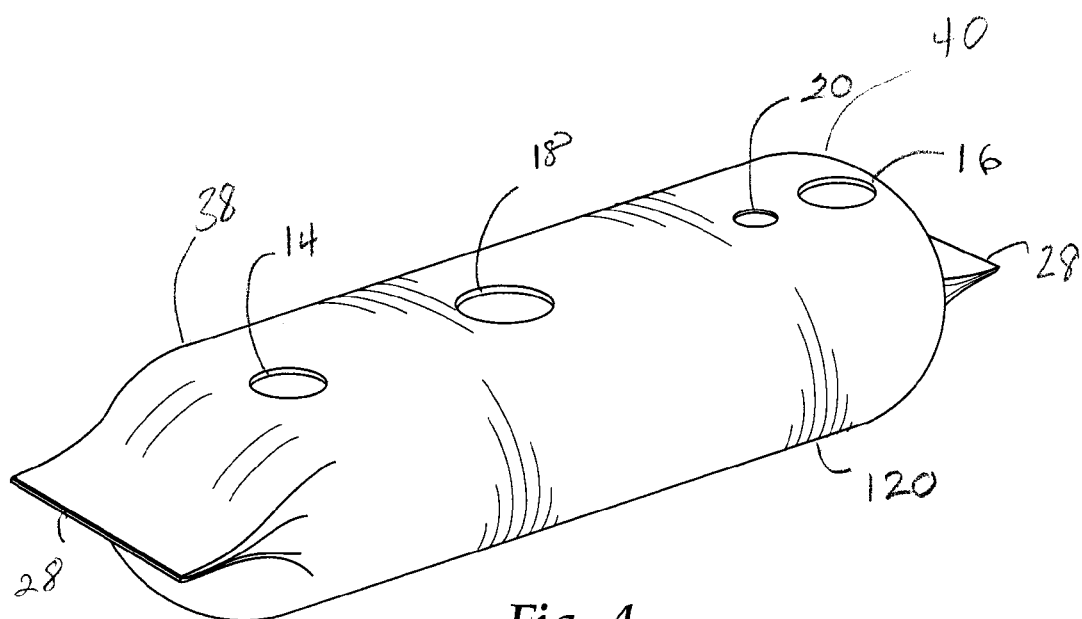
FIG. 4 is a perspective view of an alternative configuration of the substantially flexible bladder.
Figure 4A:
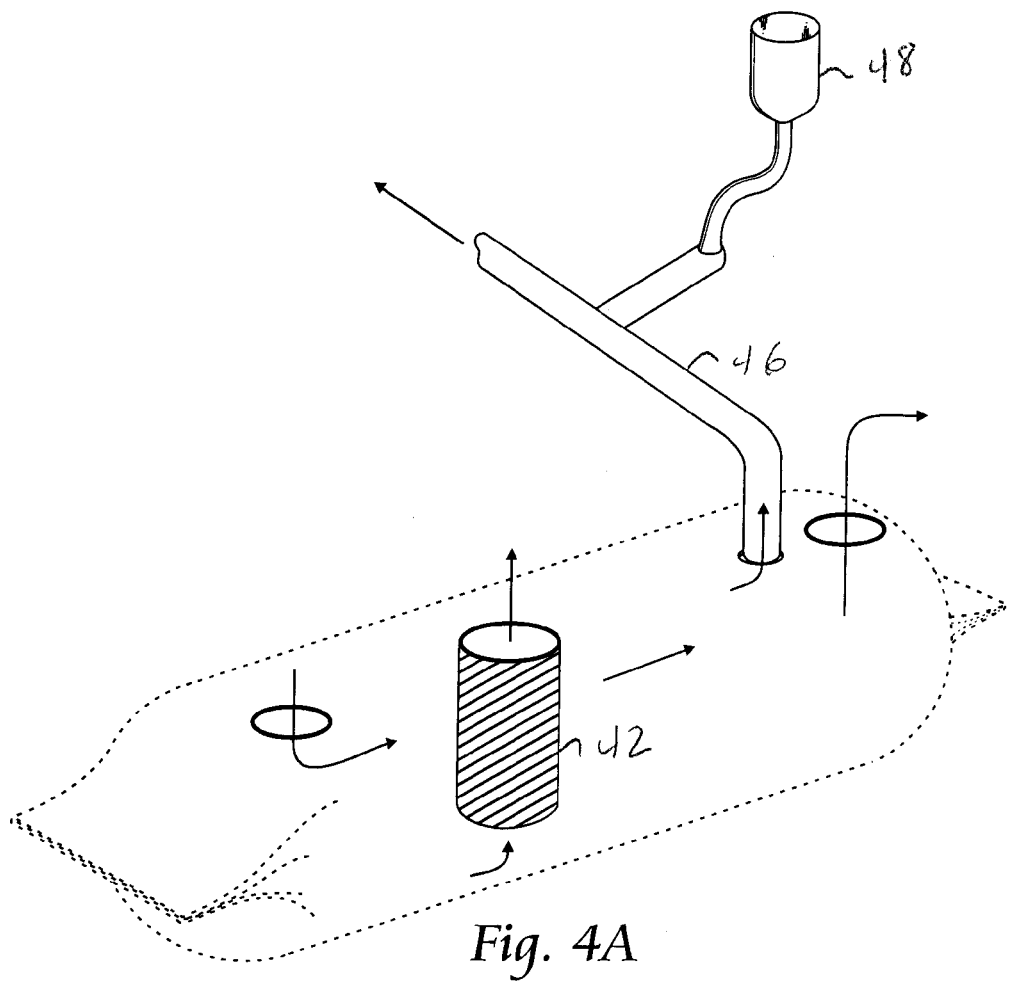
FIG. 4A is an interior operational perspective view of the bladder of FIG. 4, illustrating by arrows the movement of animal waste into the waste inlet and out the digester effluent outlet and release of biogas through the biogas outlet pipe connected to the exemplary manometer of FIG. 2 and removal of sludge through the sludge drawdown tube and sludge access port.

The shape and size of the bladder may be limited by manufacturing concerns. A substantially rectangular, pillow-shaped bladder 12 is shown in FIGS. 1 and 3-3B. The bladder may also be substantially cylindrical as shown in FIGS. 4-4A. While not wishing to be bound to any shape or size, the bladder may be manufactured to maximize the distance between the waste inlet and the digester effluent outlet. The bladder 12 and 120 may have about a 3 to 1 to about a 5 to 1 length/width ratio, preferably a 3:1 length:width ratio.

The bladder 12 and 120 is sized to maintain critical bacterial populations and to accommodate varying waste volumes from livestock farms. The sizing is based on parameters such as Hydraulic Retention Time (HRT) and Loading Rate. These are determined by seasonal temperature. Waste must be held in the digester for a period of time for digestion to occur. Hydraulic Retention Times may be increased depending on uncertainties of waste volume encountered at the livestock farms and/or seasonal fluctuations in local ambient temperature. If the local ambient temperature is lower than about 65 degrees Fahrenheit, hydraulic retention times may have to be increased. The ambient anaerobic digestion bladder may be sized based on the following table to maintain the bacterial population to treat and stabilize wastes where the design operating volume shall be based either on the maximum daily volatile solids (VS) loading rate per 1,000 ft$^3$, or the minimum hydraulic retention time (HRT) adequate for methane production, whichever is greater. The maximum daily VS loading rate and the minimum HRT may be selected from the values in Table 1 below according to latitude. In cases where systems may be located in between the specified latitudes, the higher latitude parameter may be selected.

TABLE 1

| Latitude (N° & S°) | Min. HRT (days) | Max. Loading Rate lbs. VS/1,000 ft.$^3$/day |
|---|---|---|
| 35 | 40 | 10 |
| 30 | 35 | 12 |
| 20 | 26 | 18 |
| 10 | 24 | 20 |
| 0 | 23 | 22 |

There are two events that affect sizing: Volatile solids and process water. Both of these can be variable with process water having the most variability. If water use is low, then the system is sized on loading rate and is loading rate limited. If water use is high, then the system will be HRT limited and will be comparatively much larger than a loading rate limited system. The more water used, the larger the volume requirement. The formula for sizing the bladder is as follows:

A=Total VS Lbs. The value for A may be determined from a table such as the exemplary Table 2 shown below for pigs in the United States or from other representative methods including sampling and analysis of materials.

TABLE 2

| Animal Type | LbsVS/day/1,000 lbs live weight |
|---|---|
| Grower (40-220 lb) | 5.4 |
| Gestating Sow | 2.13 |
| Lactating Sow | 5.4 |
| Boar | 1.7 |
| Nursery (0-40 lb) | 8.8 |

(USDA/NRCS Field Waste Management Handbook). It is to be appreciated that persons skilled in the art may make known reference to similar tables to determine the value for B=Total volume waste cubic feet/day
C=Cubic feet process water/day
Where:
(B+C)×HRT (for latitude)=D (total volume)
Then check loading rate by: A/D
If the loading rate exceeds maximum as set forth in Table 1, increase HRT until condition is satisfied.

In a preferred form as shown in FIGS. 1 and 4, the bladder has one waste inlet, one digester effluent outlet, one biogas outlet, and one or more sludge access ports. As shown in FIG. 3, the substantially rectangular bladder 12 may include an internal baffle 30 defining a U-shaped interior having an inlet side 32 and an outlet side 34. The U-shaped interior typically has a better footprint (more compact) for the farms with space constraints or desire inlets and outlets on the same side dependent on the configuration of the farm waste handling system. As shown in FIG. 1, the waste inlet 14 and sludge access port 18 are defined in the inlet side 32 of the bladder 12 and the digester effluent and biogas outlets 16 and 20 are defined in the outlet side 34 of the bladder. The waste inlet 14 and digester effluent outlet 16 may be fitted respectively with a corresponding cap 36 as shown in FIG. 3 for protection during shipment and to hold water and pressure during testing of the bladder. The caps may be removed when installed for use.

In the substantially cylindrical bladder 120 as shown in FIGS. 4 and 4A, the waste inlet 14 may be on a first end 38 with the digester effluent outlet 16 on a second end 40 of the top surface 22. The biogas outlet 20 may be substantially proximate the digester effluent outlet 16 as shown in FIG. 4A and the sludge access port 18 in substantially the center of the top surface 22 of the cylindrical bladder 120.

The waste inlet 14, digester effluent outlet 16, sludge access port 18, and biogas outlet 20 in the top surface of the bladder 12 and 120 make them accessible for maintenance, etc. with the bottom surface 26 of the bladder on the ground or floor.

The one or more sludge access ports 18 may be used to withdraw sludge from the bladder 12 and 120. As shown in FIGS. 3 and 4A, a sludge drawdown tube 42 may extend inwardly into the substantially flexible bladder 12 and 120 from each of the sludge access ports 18. The sludge may be separated from the liquid fraction (i.e. the digester effluent) and removed through the one or more sludge access ports 18 from the one or more drawdown tubes 46. In smaller bladders with volumetric capacities of about 3,000 ft$^3$, there would typically be one sludge access port with a corresponding sludge drawdown tube about 2 to about 3 feet from the waste inlet or about ¼-⅓ down the length of the bladder from the waste inlet. As the volumetric capacity of the bladder increases, the number of sludge access ports and corresponding sludge drawdown tubes may increase. As the waste sits in the bladder, sludge accumulates at the bottom of the bladder. The sludge access port may include an adapter (not shown) for receiving a flex hose (not shown) from a pump (not shown) to mechanically remove the solids. Alternatively, solids may be removed manually through the sludge access port with a screened scoop/dipper or other simple hand operated removal device. The diameter of the one or more sludge access ports may be about 2 to about 6 inches. A substantially gas tight cap 44 as shown in FIG. 3 on the one or more sludge access ports 18 may be removed to manually lift or pump out the sludge. Typically, the solids in cow (ruminant) manure would be separated from the liquid fraction prior to conveyance through the waste inlet 14 as cow manure solids float and may bypass the sludge drawdown tubes. For pig manure, the drawdown tubes may typically be used to draw off the sludge or solids.

Figure 2:
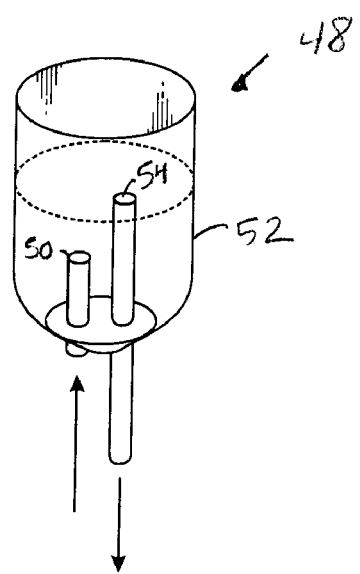
FIG. 2 is a perspective view of an exemplary manometer for the bladder of FIG. 1.
Figure 10:
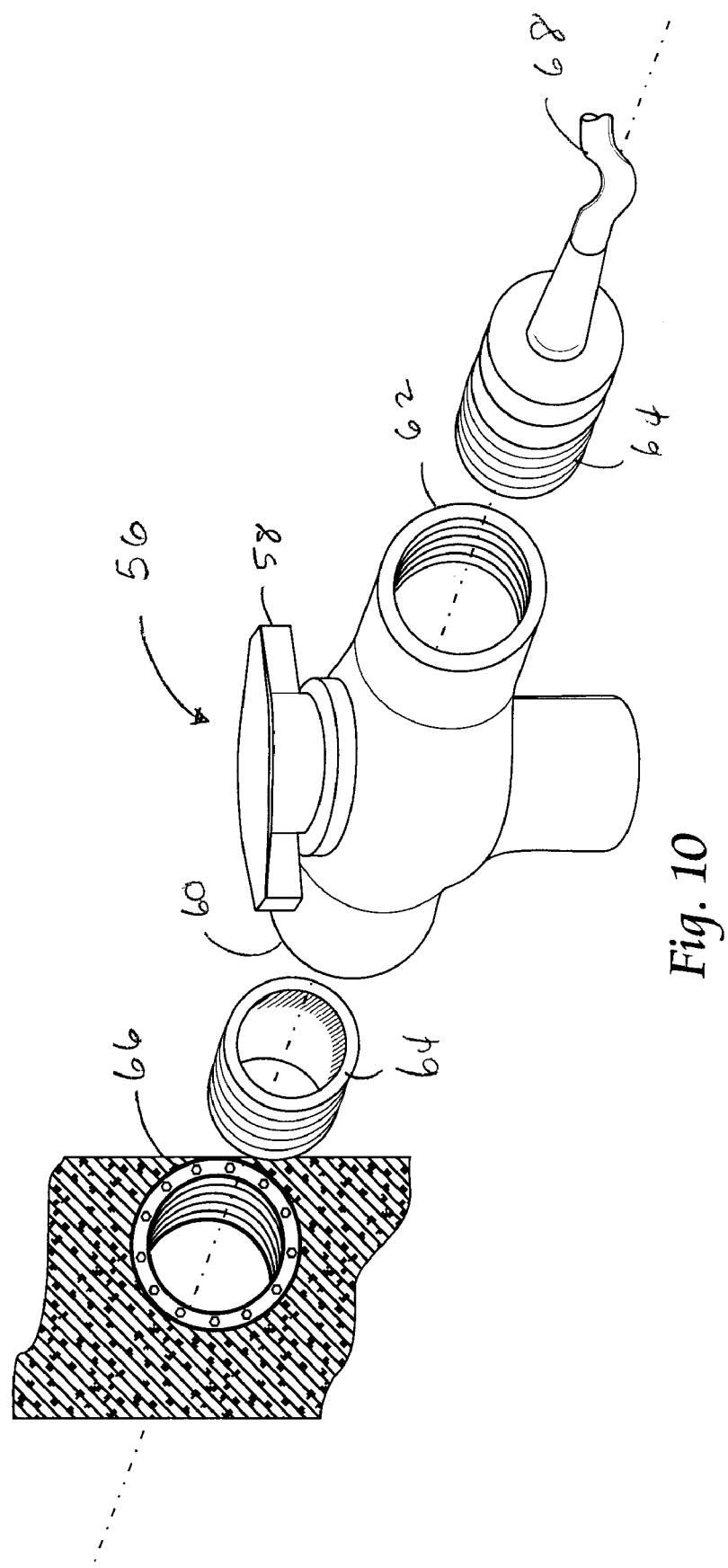
FIG. 10 is an assembly view of a 3-way ball valve connecting to the biogas outlet in a substantially flexible bladder or biogas storage container.

The biogas generated in the bladder 12 and 120 from anaerobic digestion of the animal waste may be discharged through the biogas outlet 20 into a biogas outlet pipe 46 for transmission to one or more biogas use devices (not shown) and/or the one or more biogas storage containers 24 and 240 as hereinafter described. The bladder 12 and 120 may be pressurized (weighted) by biogas production so biogas will flow without biogas handling equipment such as blowers and compressors. Pressure within the bladder may be regulated through a manometer 48. The exemplary manometer shown in FIG. 2 may be used and includes a first flexible tube 50 filled with water and an attached bottle 52. The bottle is configured to self-regulate pressure by displacing water from an entrance connection allowing biogas to vent from a second tube 54 extending above the water level. As pressure within the bladder falls, the water returns back into the manometer at a pre-selected pressure, about 24 inches water column. Although a manometer suitable for small farms has been described, it is to be appreciated that other manometer types may be used within the confines of the invention. The manometer may come off the bladder 12 and 120 or a biogas storage container as hereinafter described A ball valve 56 such as shown in FIG. 10 may regulate the flow of gas out of the bladder and into the biogas use device and/or into and out of the biogas storage container(s) as hereinafter described. The ball valve typically remains in the open position. The ball valve may also serve as a condensate drain. The ball valve 56 includes a T-handle 58 and has an inlet and outlet 60 and 62 that may each be internally threaded as shown in FIG. 10 for threadably engaging with a male adapter 64, typically a bushing. The inlet 60 of the ball valve may be coupled to a bulkhead fitting 66 in the biogas outlet of the bladder and/or biogas storage container. The adapter 64 at the outlet 62 of the ball valve may be coupled to a nipple 68 for attachment to a gas hose (not shown) for transmitting biogas to one or more biogas use devices. The valve materials may preferably be constructed of non-corrosive materials, such as PVC or the like. Although a 3-way ball valve is shown and described, it is to be appreciated that other types of valves may be used within the confines of the invention.

Biogas use devices (not shown) include flares, boilers, absorption coolers, engine generators, cook stoves, gas lighting or the like. Other biogas use devices are selected on a farm by farm basis dependent upon the goals of the farmer i.e. odor control, electrical energy, heat, co-generation, cooking, lighting. The biogas may be delivered to the biogas use device when the user turns on the device.

The biogas may also be stored in one or more external biogas storage containers 24 and 240. Stored biogas may be used on an intermittent basis for cooking, lighting, heating or the like. An exemplary external substantially cylindrical biogas storage container 24 is shown in FIGS. 6 and 6A with a top portion and a bottom portion 70 and 72. The top and/or bottom portions may be structurally reinforced with a plywood wafer 74 or the like to substantially prevent collapse of the container when biogas is discharged. The wafer helps the biogas storage container maintain its shape and provides for more even compression of the biogas storage container. The wafer may be about ¼ inch to about ¾ inches thick and seam sealed in the top and bottom portions of the container. A weight 76 such as a sandbag or the like may be supported on the wafer-reinforced top and bottom portions of the container to keep substantially constant positive pressure on the container to transmit gas. The container may further include a plurality of handles 78 to assist in the transport of the biogas storage containers as hereinafter described. The handles may be affixed through the wafer and/or container material.

The exemplary cylindrical biogas storage container 24 may be about 6 feet high with a diameter of about 4 feet but other sizes and shapes may be used within the confines of the invention. The external biogas storage container may be constructed of the same or different flexible geo-membrane material as the bladder. The biogas storage container may inflate with biogas production and deflate when biogas is used. The biogas storage container 24 has an opening 80 proximate the lower end of the container. The opening 80 is in fluid communication with the biogas outlet in the substantially flexible bladder. The opening 80 may be fitted with the bulkhead fitting 66 as shown in FIG. 10 for coupling the biogas storage container 24 to the low pressure 3-way ball valve 56.

Figure 8:
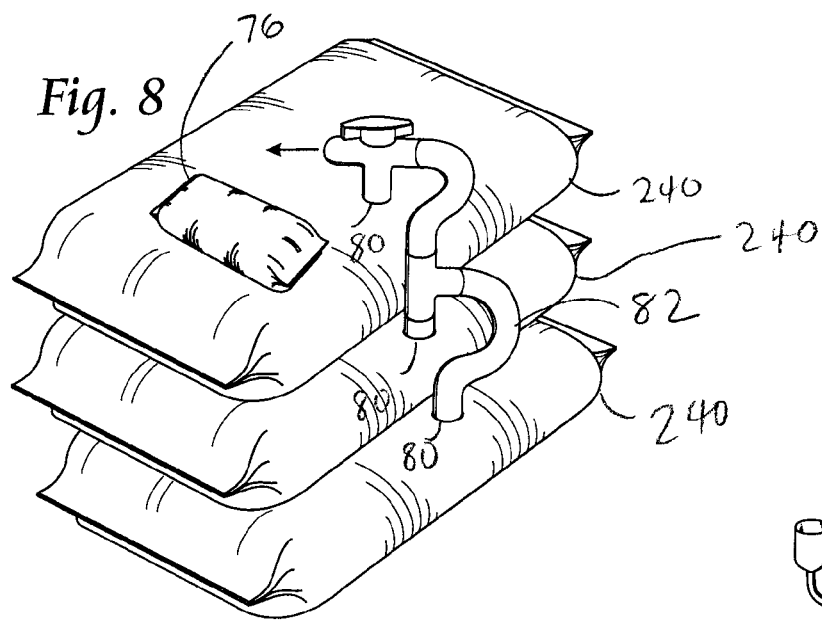
FIG. 8 is a perspective view of a plurality of exemplary stacked substantially rectangular biogas storage containers, illustrating the removal of biogas therefrom.

In an alternative embodiment, the one or more external biogas storage containers 240 may be substantially rectangular as shown in FIG. 8. The substantially rectangular biogas storage containers may be stacked and each includes the opening 80 in a top surface thereof for transmitting biogas through an interconnected gas pipe 82 to the ball valve 56. The weight 76 may be placed on the top surface of the uppermost container. The manometer 48 may be used with the biogas storage containers (not shown) to regulate pressure therein.

Where biogas may be sold, distributed and used off-site, the biogas storage containers may be portable. When used in this manner, the handles may be used to more easily transport the biogas storage containers. The biogas storage containers may be filled, transported, and refilled. This embodiment is particularly suitable for large digester systems where biogas is transported for local use such as cooking and lighting. Although portable biogas storage containers have been described for use with the anaerobic digester bladder, it is to be appreciated that such portable biogas storage containers may be used with other anaerobic digester systems.

For a gas distribution set-up, large digesters are required with multiple biogas storage containers for transfer to customers. The one or more external biogas storage containers 24 and 240 may be stored in a support platform 84 as shown in FIG. 7 which rests on a concrete floor or the like in order to support the containers. The support platform 84 may have flexible supports 86 for substantially maintaining the biogas storage container(s) 24 in an upright position. For the exemplary biogas storage containers shown in FIG. 6, the openings may be circular to correspond to the substantially cylindrical shape of the biogas storage containers. It is to be appreciated that when other shapes are used for the external biogas storage containers, the shape and size of the openings in the support platform may be changed to correspond to those shapes and sizes. For example, openings in the support platform shown in FIG. 7 may support the plurality of exemplary stacked substantially rectangular biogas storage containers shown in FIG. 8. The number of biogas storage containers is determined on daily gas use needs and gas output from the digester.

Figure 5:
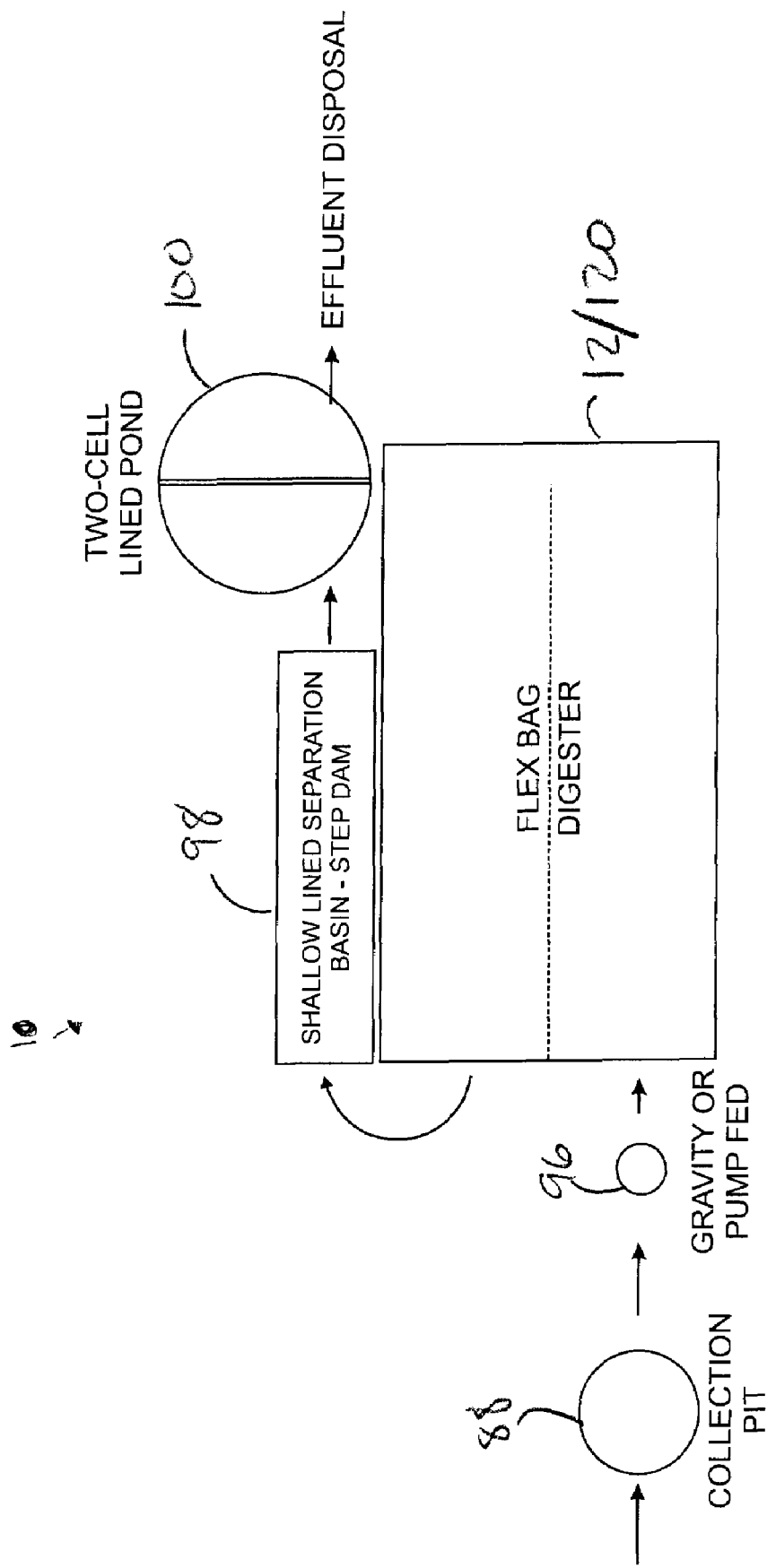
FIG. 5 is a schematic of an exemplary anaerobic digester system, illustrating use of the substantially flexible bladder as the primary waste treatment.
Figure 9:
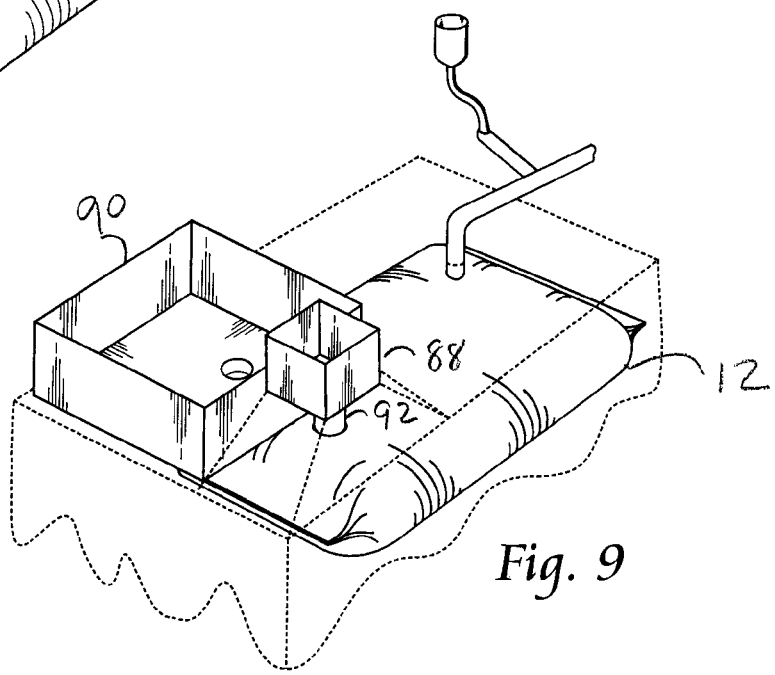
FIG. 9 is a perspective view of an alternative embodiment of the anaerobic digester system, illustrating a floor in dotted lines with the substantially flexible bladder under the floor and a displacement tank and inlet basin in fluid communication therewith.
Figure 9A:
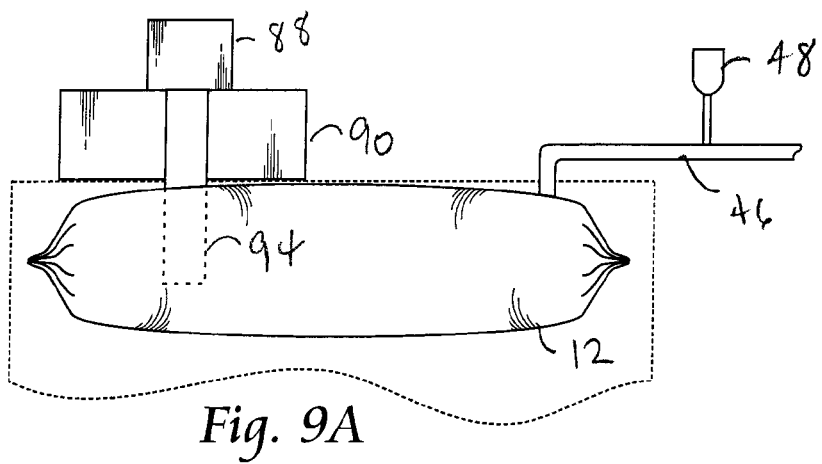
FIG. 9A is a side view of the anaerobic digester system of FIG. 9.

In an alternative embodiment as shown in FIGS. 9-9A, the biogas may be stored inside the substantially flexible bladder for use onsite. When used in this manner, the system further comprises an inlet basin 88 for receiving and conveying waste into the bladder and an external displacement tank 90. The external displacement tank 90 is designed to hold waste that is displaced by internal bladder pressure. The inlet basin 88 is typically small, about $\frac{1}{30}$ the size of the bladder volume. A pipe 92 from the inlet basin feeds waste into the waste inlet 14 in the bladder. A displacement tank pipe 94 from the displacement tank may extend downwardly from an opening in the bottom of the displacement tank through the digester effluent outlet 16 and into the bladder as shown in FIG. 9A. The length of the pipe 94 extending into the bladder from the displacement tank should be long enough to make a gas seal to substantially prevent gas from leaking out as is well known in the art. The displacement tank may be substantially shallow. The volume of the displacement tank may be about $\frac{1}{3}$ to about $\frac{1}{2}$ the volume of the bladder. As biogas is produced inside the bladder, the waste is pushed out of the digester effluent outlet into the external displacement tank and when biogas is used, the displaced waste flows back into the bladder through the digester effluent outlet. The external displacement tank may be constructed of concrete, bricks, steel, or geo-membrane materials depending on local conditions and cost. The inlet basin and displacement tank may be round, square, rectangular, a combination thereof or other shapes. The displacement tank pipe 94 may be flexible and durable, about 1 foot to about 4 feet long. A semi-rigid pipe may extend downwardly from the bottom of the inlet basin to the waste inlet in the bladder. The inlet basin bottom may be set at the wall height level of the displacement tank where the displacement tank floor may be set at the top elevation of the bladder. The inlet basin is represented in FIG. 5 as the "collection pit."

In use, the bladder(s) may be factory fabricated and field installed. As shown in FIG. 5, the animal waste may be conveyed with a water flush from a tip bucket or hose or the like to an inlet basin 88 or other collection pit from where it may be conveyed by gravity, diaphragm pump 96 or the like to the bladder (the so-called "flex bag digester"). The animal waste enters the bladder 12 and 120 at the waste inlet 14 and flows through the bladder 12 and 120 and undergoes anaerobic bacterial digestion before exiting as digester effluent through the digester effluent outlet 16 for further processing or land application. The bladder 12 and 120, for primary waste treatment, may be complemented by other structures for secondary and tertiary waste treatments (i.e. further processing). By way of example only, and as shown in FIG. 5, the digester effluent may be conveyed through gravity or other conveyance to a shallow lined separation basin-step dam 98, then to a two cell lined pond 100 prior to effluent disposal. The shallow lined separation basin and two cell lined pond are exemplary structures and are not limiting within the confines of the invention. "Effluent disposal" as used herein means further processed or land applied. The solids in the waste may be removed prior to conveyance into the bladder or may be removed through the one or more sludge drawdown tubes. The biogas generated in the bladder may be used by the one or more biogas use devices (not shown) and/or stored within the bladder equipped with a displacement tank and/or stored in one or more external biogas storage containers.

From the foregoing, it is to be appreciated that the novel anaerobic digester system and method may simply, reliably, and inexpensively treat animal waste with biogas production and recovery in warm climates where minimum temperatures are about 65° F. or higher. Such system and method help control air and water pollution from livestock waste, protect public health and offer an opportunity for the waste to be used as a renewable energy resource. The sizing method substantially permits biological stabilization of ambient temperature anaerobic digesters treating dilute animal wastes and other dilute high strength wastes in regions that lie between 35° north and south latitudes The digester may be factory fabricated and field installed making it particularly well suited for the small farm having limited resources.

Although a particular embodiment of the invention has been described in detail for purposes of illustration, various modifications may be made without departing from the spirit and scope of the invention. Accordingly, the invention is not to be limited, except as by the appended claims.

I claim:

1. A method for anaerobically digesting dilute animal waste with biogas production, comprising the steps of:
   Conveying dilute animal waste containing through one or more waste inlets in a substantially flexible bladder;
   Maintaining the dilute animal waste in the substantially flexible bladder at an average ambient temperature of 65 degrees Fahrenheit or greater for a period of time for digestion of the dilute animal waste;
   Removing digester effluent from the substantially flexible bladder through one or more digester effluent outlets in the substantially flexible bladder;
   Providing a displacement tank in fluid communication with at least one of the one or more digester effluent outlets; and
   Storing biogas within the substantially flexible bladder by displacing animal waste therein through the at least one of the one or more digester effluent outlets into the displacement tank.

2. The method of claim 1, wherein the animal waste is received into the substantially flexible bladder from an inlet basin having a size substantially smaller than the substantially flexible bladder.

3. The method of claim 1, further comprising the step of recovering the biogas produced within the substantially flexible bladder.

4. The method of claim 1, further comprising the step of recovering solid waste from the substantially flexible bladder through one or more sludge access ports in the substantially flexible bladder.

5. The method of claim 1, further comprising the step of mechanically separating solid animal waste from liquid animal waste.

6. The method of claim 5, wherein the step of mechanically separating solid animal waste from liquid animal waste occurs prior to the conveying step.

7. The method of claim 1, wherein recovering the biogas produced within the bladder comprises transmitting biogas from the substantially flexible bladder through one or more biogas outlets in the substantially flexible bladder to at least one biogas use device, at least one biogas storage container or combination thereof.

8. The method of claim 1, wherein the substantially flexible bladder is constructed of a reinforced geo-membrane material.

9. The method of claim 1, further comprising providing a longitudinal baffle inside the substantially flexible bladder.

10. A method for anaerobically digesting animal waste with biogas production at an average ambient temperature of 65 degrees Fahrenheit or greater, comprising the steps of:
   Conveying animal waste through one or more waste inlets in a substantially flexible bladder sized to maintain the greater of a minimum HRT or daily volatile solids loading rate per 1000 ft$^3$;
   Maintaining the animal waste in the substantially flexible bladder for a period of time for anaerobic digestion of the animal waste;
   Removing solid animal waste from the substantially flexible bladder;
   Removing digester effluent from the substantially flexible bladder through one or more digester effluent outlets in the substantially flexible bladder;
   Providing a displacement tank in fluid communication with at least one of the one or more digester effluent outlets; and
   Storing biogas within the substantially flexible bladder by displacing animal waste therein through the at least one of the one or more digester effluent outlets into the displacement tank.

11. The method of claim 10, further comprising the step of recovering the biogas produced within the substantially flexible bladder.

12. The method of claim 10, further comprising the step of removing the solid animal waste from the substantially flexible bladder through one or more sludge access ports in the substantially flexible bladder.

13. The method of claim 10, wherein recovering the biogas produced within the bladder comprises transmitting biogas from the substantially flexible bladder through one or more biogas outlets in the substantially flexible bladder to at least one biogas use device, at least one biogas storage container or combination thereof.

14. The method of claim 10, further comprising the step of:
   Providing a displacement tank in fluid communication with at least one of the one or more digester effluent outlets; and
   Storing biogas within the substantially flexible bladder by displacing animal waste therein through the at least one of the one or more digester effluent outlets into the displacement tank.

15. The method of claim 10, wherein the substantially flexible bladder is constructed of a reinforced geo-membrane material.

* * * * *